United States Patent [19]

Rufer et al.

[11] 4,053,472
[45] Oct. 11, 1977

[54] 2-(5-NITRO-2-IMIDAZOLYL)-BENZIMIDAZOLES

[75] Inventors: Clemens Rufer; Eberhard Schröder; Hans-Joachim Kessler, all of Berlin, Germany

[73] Assignee: Schering Aktiengesellschaft, Berlin & Bergkamen, Germany

[21] Appl. No.: 287,852

[22] Filed: Sept. 11, 1972

Related U.S. Application Data

[63] Continuation-in-part of Ser. No. 29,705, April 17, 1970, abandoned.

[30] Foreign Application Priority Data

Apr. 19, 1969 Germany .......................... 1920635

[51] Int. Cl.$^2$ .................. C07D 403/04; C07D 405/14
[52] U.S. Cl. ........................ 544/139; 260/239 B; 260/268 BC; 260/268 R; 260/293.6; 260/293.79; 548/327; 548/339; 260/326.47; 260/326.5 L; 260/326.85; 260/570.5 P; 424/248.55; 424/250; 424/267; 424/273 R
[58] Field of Search .................. 260/309.2, 247.5 B, 260/293.6, 268 BC

[56] References Cited

U.S. PATENT DOCUMENTS

| | | | |
|---|---|---|---|
| 3,309,378 | 3/1967 | Dunn | 260/309.2 |
| 3,322,783 | 5/1967 | Dunn | 260/309.2 |
| 3,478,046 | 11/1969 | Sarett et al. | 260/309.2 |

FOREIGN PATENT DOCUMENTS 1,920,635  10/1970  Germany .......................... 260/309.2

OTHER PUBLICATIONS

Rufer et al., Abandoned Application Ser. No. 29,705, pp. 1, 2, 3a, 3b, 13 & 14 (filed Apr. 17, 1970).
Dunn et al., J. Med. Chem., vol. 9, pp. 751–753 (1966).

*Primary Examiner* — Natalie Trousof
*Attorney, Agent, or Firm* — Millen & White

[57] ABSTRACT

2-(5-Nitro-2-imidazolyl)-benzimidazoles of the formula

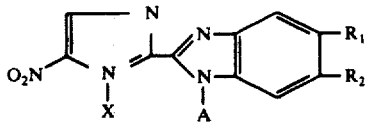

wherein $R_1$ and $R_2$ are H, halo, alkyl, alkoxy, nitro, trifluoromethyl or carboxy; A is H, alkyl, hydroxyalkyl or an ester thereof, haloalkyl, phenyl or a tertiary aminoalkyl group; and X is alkyl, hydroxyalkyl or an ester thereof, are antimicrobials, especially against *Trichomonas vaginalis*.

14 Claims, No Drawings

2-(5-NITRO-2-IMIDAZOLYL)-BENZIMIDAZOLES

BACKGROUND OF THE INVENTION

This is a continuation-in-part of application Ser. No. 29,705, filed Apr. 17, 1970, now abandoned.

Holan et al., J. Chem. Soc. (London) C, 1967, pages 33-9, disclose benzimidazole derivatives to thiophene and pyrrole. U.S. Pat. No. 3,478,046 discloses benzimidazoles substituted at the 2-position by heterocyclic rings which do not include imidazole nor a nitro substituent on the heterocyclic ring. U.S. Pat. No. 3,222,783 and 3,309,378 disclose benzimidazoles substituted at the 2-position by nitropyrryl and nitrothienyl, respectively. Dunn et al., J. Med. Chem., Vol. 9, pp. 751-3 (1966) describes the anti-trichomonal and anti-helmintic activities of such compounds.

SUMMARY OF THE INVENTION

This invention relates to novel 2-(5-nitro-2-imidazolyl)-benzimidazoles having antimicrobial activity and which exhibit greater activity against *Trichomonas vaginalis* than metronidazole, of the formula

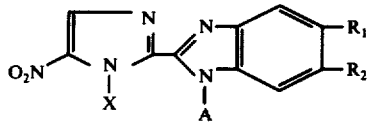
(I)

wherein A is hydrogen, alkyl of 1 to 5 carbon atoms, hydroxyalkyl of 2 to 5 carbon atoms or an acyl ester thereof of an alkanoic acid or a physiologically acceptable carbocyclic aryl acid of up to 12 carbon atoms, the aryl acid having 1-2 separate or fused rings, halo-alkyl of 2 to 5 carbon atoms, phenyl and aminoalkyl of the formula

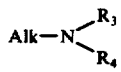

wherein Alk is alkyl of 2 to 5 carbon atoms and

is dialkyl amino, pyrrolidino, piperidino, homopiperidino, morpholino, piperazino or the corresponding heterocyclic rings substituted on a ring carbon atom by alkyl, or piperazino substituted on the 4-position nitrogen atom by alkyl or hydroxyalkyl of 2-5 carbon atoms or an ester thereof of an alkanoic acid of 1-5 carbon atoms, alkyl in each instance being of 1 to 5 carbon atoms; and $R_1$ and $R_2$, which can be identical or different, each are hydrogen, halogen, alkyl of 1 to 4 carbon atoms, alkoxy of 1 to 4 carbon atoms, nitro, trifluoromethyl and carboxy and X is alkyl of 1 to 5 carbon atoms, hydroxyalkyl of 2 to 5 carbon atoms, or a corresponding acyl ester thereof of an alkanoic acid or a physiologically acceptable carbocyclic aryl acid of up to 12 carbon atoms, the aryl acids having 1-2 separate or fused rings, both in free base form and in the form of their physiologically acceptable salts thereof, either with acids, or with bases when an acid group is present in the molecule.

DETAILED DISCUSSION

Examples of X which are alkyl are methyl, ethyl, isopropyl, butyl, sec.-butyl, iso-butyl and tert.-butyl, X can also contain unsaturation or a greater number of carbon atoms and equivalents of the compounds of this invention are those wherein X is hexyl, heptyl, octyl, nonyl, decyl, ethenyl, ethynyl, allyl, propynyl, 1-methylallyl, crotyl, butadienyl, 2-octenyl, 6-octenyl, etc., preferably alkyl of 1-4 carbon atoms containing a single unsaturation, preferably a double bond in the β-position.

Examples of A and X which are hydroxyalkyl are β-hydroxyethyl and γ-hydroxypropyl; of halo-alkyl are β-chloroethyl and β-bromoethyl; of acyloxyalkyl are β-acyloxyethyl and γ-acyloxypropyl wherein acyl is the acyl radical of an alkanoic acid of 1-5 carbon atoms or benzoic acid.

Examples of

are dimethylamino, methylethylamino, diethylamino, methyl-n-propylamino, dipropylamino, diisopropylamino, methylisobutylamino, di-n-butylamino, pyrrolidino, 2-methylpyrrolidino, 2,5-dimethylpyrrolidino, 3-ethylpyrrolidino, piperidino, 2-methylpiperidino, homopiperidino, 3-methylhomopiperidino, morpholino, 2,6-dimethylmorpholino, piperazino, N-methylpiperazino, N-ethylpiperazino, β-hydroxyethylpiperazino and β-acetoxyethylpiperazino.

Preferred classes of compounds of this invention are those defined by Formula I wherein:

a. X is hydroxyalkyl, especially hydroxyethyl, or an ester thereof as defined above, especially those wherein A is H or alkyl as defined above, preferably methyl or ethyl.

b. X is alkyl, preferably of 1 to 4 carbon atoms, especially methyl or ethyl, and A is hydroxyalkyl, especially hydroxyethyl, or an ester thereof, haloalkyl, especially haloethyl, or aminoalkyl, especially aminoethyl, as defined above.

c. X is alkyl as defined above, preferably methyl or ethyl, and A is H or alkyl, preferably methyl or ethyl.

d. A is

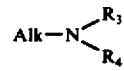

as defined above, especially wherein Alk is $C_2H_4$ or $C_3H_6$ and

is dimethylamino, diethylamino, pyrrolidino or morpholino particularly those of (a) and (b).

e. X is alkyl of 1-4 carbon atoms, more preferably methyl or ethyl, and A is as defined in (d).

f. each of (a) – (e) inclusive, wherein one or both of $R_1$ and $R_2$ are H or $CH_3$.

g. physiologically acceptable acid addition salts of groups (a) – (f), inclusive. Suitable acids for the formation of acid addition salts are, for example: hydrochloric acid, sulfuric acid, acetic acid, lactic acid, succinic acid and tartaric acid. Preferred acids are those which form physilogically acceptable acid addition salts. Others can be employed for isolation, purification and/or characterization purposes.

Other examples of equivalents of the compounds of this invention are those otherwise corresponding to Formula I having one or more, usually not more than four and preferably not more than three, simple substituents on the A group, when A is alkyl, or on the aryl carbocyclic acid group when A or X is esterified hydroxyalkyl, e.g., chloro and fluoro, lower-alkyl, including methyl, ethyl, propyl and octyl, trifluoromethyl, trichloromethyl, lower-alkoxy, including methoxy and ethoxy, aryloxy and aralkoxy, including benzyloxy and phenoxy, carboxy, nitro, sulfato, acetamido, aryl, including phenyl and aralkyl, including benzyl, wherein aryl in each instance is as defined above. Preferably, so that the activity and characteristic structure is predominantly that of a 2-(5-nitro-2-imidazolyl)-benzimidazole, the sum of the molecular weights of these substituents is less than 200 and preferably less than 150 and preferably contain a total of less than 8 carbon atoms and less than 4 heteroatoms.

Examples of compounds of this invention in which X or A is an esterified hydroxy alkyl group are those wherein the ester is that of an acid of up to 14, preferably up to 10 carbon atoms and 0 to 4, preferably 0 to 1, rings and 0 to 3, preferably 0 to 2, heteroatoms. Examples are esters of formic, acetic, propionic, butyric, octanoic and undecylic acid, of an aryl or alkaryl acid, e.g., benzoic, 2, 3, or 4-methylbenzoic, 2,3-, 2,4-, 2,5-, 2,6-, 3,4- and 3,5-dimethyl benzoic, ethylbenzoic, 2,4,6-trimethylbenzoic, 2,3,4-trimethoxybenzoic, 2,4,6-triethylbenzoic, α-naphthoic, 3-methyl-α-naphthoic, an aromatic hydroxy acid, e.g., salicylic acid, an aromatic aminoacid, e.g., para-aminosalicylic, para-aminobenzoic. Equivalent esters are those of other acids, e.g., carbamic acids, e.g., carbamic acid, phenylcarbamic, n-butylcarbamic, dimethylcarbamic, diethylcarbamic, allophanic, or a heterocyclic acid, e.g., β-furylcarboxylic, N-methylpyrrolidyl-2-carboxylic, α-picolinic, indole-2-carboxylic, 6-hydroxy-indolyl-3-acetic, N-methylmorpholyl-2-carboxylic, lysergic, pyrrolyl-2-carboxylic or other acyl acid.

Specific examples of compounds of this invention, some of which are described in the examples hereinafter, include 1-(2-morpholinoethyl)-2-(5-nitro-1-methyl-2-imidazolyl)-benzimidazole; 1-(2-pyrrolidinoethyl)-2-(5-nitro-1-methyl-2-imidazolyl)-benzimidazole; 1-(2-piperidylethyl)-2-(5-nitro-1-methyl-2-imidazolyl)-benzimidazole; 1-(2-homopiperidylethyl)-2-(5-nitro-1-methyl-2-imidazolyl)-benzimidazole; 1-(2-piperazinylethyl)-2-(5-nitro-1-methyl-2-imidazolyl)-benzimidazole; 1-(2-N'-methyl-piperazinylethyl)-2-(5-nitro-1-methyl-2-imidazolyl)-benzimidazole; 1-(2-N'-hydroxyethyl-piperazinylethyl-2-(5-nitro-1-methyl-2-imidazolyl)-benzimidazole; 1-(2-N'-acetoxyethyl-piperazinylethyl)-2-(5-nitro-1-methyl-2-imidazolyl)-benzimidazole; 1-(2-N'-benzoxyethyl-piperazinylethyl)-2-(5-nitro-1-methyl-2-imidazolyl)-benzimidazole; 1-(2-acetoxyethyl)-2-(5-nitro-1-methyl-2-imidazolyl)-benzimidazole; 1-(2-hydroxyethyl)-2-(5-nitro-1-methyl-2-imidazolyl)-benzimidazole; 1-(2-(benzoxyethyl)-2-(5-nitro-1-methyl-2-imidazolyl)-benzimidazole; 1-(2-chloroethyl)-2-(5-nitro-1-methyl-2-imidazolyl)-benzimidazole and the corresponding 5-methyl, 5-chloro, 5-methoxy, 5-nitro, 5-trifluoromethyl and 5-carboxy substituted compounds corresponding to each of the above, 1-(2-morpholinoethyl)-2-(5-nitro-1-ethyl-2-imidazolyl)-benzimidazole; 1-(2-pyrrolidinoethyl)-2-(5-nitro-1-ethyl-2-imidazolyl)-benzimidazole; 1-(2-piperidylethyl)-2-(5-nitro-1-ethyl-2-imidazolyl)-benzimidazole; 1-(2-homopiperidylethyl)-2-(5-nitro-1-ethyl-2-imidazolyl)-benzimidazole; 1-(2-piperazinylethyl)-2-(5-nitro-1-ethyl-2-imidazolyl)-benzimidazole; 1-(2,N'-methyl-piperazinylethyl)-2-(5-nitro-1-ethyl-2-imidazolyl)-benzimidazole; 1-(2-N'-hydroxyethyl-piperazinylethyl)-2-(5-nitro-1-ethyl-2-imidazolyl)-benzimidazole; 1-(2-N'-acetoxyethyl-piperazinylethyl)-2-(5-nitro-1-ethyl-2-imidazolyl)-benzimidazole; 1-(2-N'-benzoxyethyl-piperazinylethyl)-2-(5-nitro-1-ethyl-2-imidazolyl)-benzimidazole; 1-(2-acetoxyethyl)-2-(5-nitro-1-acetoxyethyl-2-imidazolyl)-benzimidazole; 1-(2-hydroxyethyl)-2-(5-nitro-1-hydroxyethyl-2-imidazolyl)-benzimidazole; 1-(2-benzoxyethyl)-2-(5-nitro-1-benzoxyethyl-2-imidazolyl)-benzimidazole; 1-(2-chloroethyl)-2-(5-nitro-1-chloroethyl-2-imidazolyl)-benzimidazole and the corresponding 5-methyl, 5-chloro, 5-methoxy, 5-nitro, 5-trifluoromethyl and 5-carboxy substituted compounds corresponding to each of the above, 1-(2-hydroxyethyl)-2-(5-nitro-1-phenyl-2-imidazolyl-benzimidazole, and the corresponding 5-methyl, 5-chloro, 5-methoxy, 5-nitro, 5-trifluoromethyl and 5-carboxy substituted compounds corresponding to each of the above.

The novel compounds can be prepared in the following manner:

a. a diamine of the formula

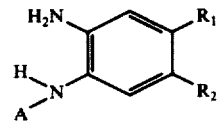

(II)

wherein A, R₁ and R₂ have the values given above, is reacted with an acid of the formula

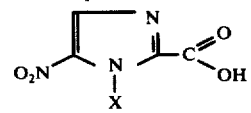

(III)

wherein X has the above-indicated meanings, or with an activated functional derivative of the acid; or b. a diamine of Formula II is reacted with an aldehyde of the formula

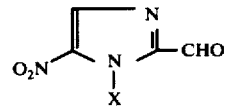

(IV)

wherein X has the values given above; or c. a compound of Formula I produced by procedure (a) or (b) is converted to another compound of Formula I by modifying a functional group present in the molecule, e.g., by converting a free OH-group into a tosylate, chloride or an amino group and/or saponifying an ester group and/or converting any thus-obtained bases or acids, respectively, into the physiologically acceptable salts thereof.

The reaction according to (a) can be conducted in the absence or in the presence of a solvent, such as, for example, alcoholic or aqueous hydrochloric acid, at room temperature or at an elevated temperature. Of the reactive functional derivatives of the acids of Formula III, the iminocarboxylic acid esters are preferably employed.

The reaction according to (b) is conducted at an elevated temperature in the presence of an oxidation agent, such as, for example, atmospheric oxygen, mercury (II) oxide, or lead tetraacetate.

The novel compounds exhibit good anti-microbial effects, especially against Trichomonas vaginalis. The table below shows the superior effect of the novel substances against Trichomonas vaginalis compared with metronidazole.

TABLE

| Compound | Minimum Inhibitory Concentration Against Trichomonas Vaginalis in γ/ml. |
|---|---|
| 1-(2-Pyrrolidinoethyl)-2-(5-nitro-1-methyl-2-imidazolyl)-benzimidazole | 0.1 |
| 1-(3-Morpholinopropyl)-2-(5-nitro-1-methyl-2-imidazolyl)-benzimidazole | 0.1 |
| 1-(3-Dibutylaminopropyl)-2-(5-nitro-1-methyl-2-imidazolyl)-benzimidazole | 0.4 |
| 2-(5-Nitro-1-ethyl-2-imidazolyl)-benzimidazole | 0.2 |
| 2-[5-Nitro-1-(2-acetoxyethyl)-2-imidazolyl]-benzimidazole | 0.2 |
| 1-(3-Dimethylaminopropyl)-2-(5-nitro-1-methyl-2-imidazolyl)-benzimidazole hydrochloride | 0.1 |
| Metronidazole (in own test) | 1.56 |

The toxicity of the novel compounds of this invention is low, i.e., greater than 200 mg/kg.

The compounds of Formula I are useful in the treatment of Trichomonas vaginalis infections. For such use, they can be formulated into conventional drug forms with the additives, carrier substances, and flavoring agents customary in pharmaceutical preparations which do not deleteriously react with the effective agents, employing conventional methods. For oral application, particularly suitable are tablets, dragees, capsules, pills, suspensions and solutions. Such compositions can employ, for example, water, alcohol, polyethylene glycols, gelatin, sucrose, lactose, amylose in solutions and suspensions and magnesium stearate, talc, starch, sugars, etc., in tablets. The concentration of the effective agent in the thus-formulated compositions is dependent on the activity of the specific compound employed, the responsiveness of the individual patient and the mode of administration. Generally, they contain about 0.05 to 2.0 g., preferably about 0.05 to 0.5 g. of a compound of this invention and 0.1 to 5 g. of a pharmaceutical carrier per unit dose.

For topical application, the compounds of this invention can be applied as a powder, solution, suspension, foam or aerosol or as vaginal tablets and suppositories. For parenteral application, aqueous or oily solutions or suspensions can be used.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

135 mg. of o-phenylenediamine in 5 ml. of methanol is allowed to stand with 248 mg. of the ethyl ester of 5-nitro-1-methyl-2-imidazolyl-iminocarboxylic acid and 0.1 ml. of 12.5N methanolic hydrochloric acid for 5 hours at 20° C. Then, the reaction mixture is cooled to −70° C.; the precipitate is vacuum-filtered and washed with cold methanol. Yield: 190 mg. of 2-(5-nitro-1-methyl-2-imidazolyl)-benzimidazole, m.p. 257° C.

EXAMPLE 2

135 mg. of o-phenylenediamine in 5 ml. of methanol and 0.085 ml. of water are treated as set forth in Example 1. Yield: 64 mg. of 2-(5-nitro-1-methyl-2-imidazolyl)-benzimidazole, m.p. 257° C.

EXAMPLE 3

324 mg. of o-phenylenediamine in 10 ml. of ethanol is boiled with 465 mg. of 5-nitro-1-methyl-2-imidazolyl aldehyde for 16 hours, with the introduction of air. The reaction mixture is cooled to 20° C., vacuum-filtered, and washed with cold ethanol. Yield: 145 mg. of 2-(5-nitro-1-methyl-2-imidazolyl)-benzimidazole, m.p. 257° C.

EXAMPLE 4

324 mg. of o-phenylenediamine in 10 ml. of ethanol is boiled with 465 mg. of 5-nitro-1-methyl-2-imidazolyl aldehyde for 2 hours. The reaction mixture is cooled to 20° C., vacuum-filtered, and the precipitate is suspended in 4 ml. of acetic acid. 700 mg. of lead(IV) acetate in 10 ml. of warm acetic acid is added thereto, and the mixture is agitated for 15 minutes at 50°–60° C. After cooling to 20° C., the mixture is diluted with 50 ml. of water, vacuum-filtered, and the precipitate is washed with water. Yield: 75 mg. of 2-(5-nitro-1-methyl-2-imidazolyl)-benzimidazole, m.p. 257° C.

Analogously, with 5-nitro-1-ethyl-2-imidazolyl aldehyde, 2-(5-nitro-1-ethyl-2-imidazolyl)-benzimidazole is obtained.

EXAMPLE 5

191 mg. of 2-(2-hydroxyethylamino)-aniline is treated as described in Example 1. Yield: 185 mg. of 1-(2-hydroxyethyl)-2-(5-nitro-1-methyl-2-imidazolyl)-benzimidazole, m.p. 176° C.

EXAMPLE 6

224 mg. of 2-(2-dimethylaminoethylamino)-aniline is treated as set forth in Example 1. Prior to cooling and vacuum-filtering, the solution is concentrated to 2 ml. Yield: 276 mg. of 1-(2-dimethylaminoethyl)-2-(5-nitro-1-methyl-2-imidazolyl)-benzimidazole as the hydrochloride, m.p. 250° C.

EXAMPLE 7

220 mg. of o-aminodiphenylamine is treated as described in Example 1, except that the reaction mixture is allowed to stand for 24 hours at 20° C. The crude product is recrystallized from isopropyl alcohol. Yield: 129 mg. of 1-phenyl-2-(5-nitro-1-methyl-2-imidazolyl)-benzimidazole, m.p. 182° C.

EXAMPLE 8

178 mg. of 4-chloro-1,2-diaminobenzene is treated as set out in Example 1. The crude product is recrystallized from dimethylformamide. Yield: 244 mg. of 5-chloro-2-(5-nitro-1-methyl-2-imidazolyl)-benzimidazole, m.p. 274° C.

EXAMPLE 9

224 mg. of 4,5-dichloro-1,2-diaminobenzene is treated as described in Example 1. Yield: 266 mg. of 5,6-dichloro-2-(5-nitro-1-methyl-2-imidazolyl)-benzimidazole, m.p. 298° C.

EXAMPLE 10

152 mg. of 3,4-diaminotoluene is treated as set forth in Example 1. The crude product is recrystallized from acetone. Yield: 177 mg. of 5-methyl-2-(5-nitro-1-methyl-2-imidazolyl)-benzimidazole, m.p. 237° C.

EXAMPLE 11

170 mg. of 4,5-dimethyl-1,2-phenylenediamine is treated as described in Example 1. The crude product is recrystallized from ethanol. Yield: 250 mg. of 5,6-dimethyl-2-(5-nitro-1-methyl-2-imidazolyl)-benzimidazole, m.p. 274° C.

EXAMPLE 12

496 mg. of 2-nitro-4-methoxyaniline is hydrogenated in 10 ml. of methanol with 75 mg. of Raney nickel in an autoclave at 120 atmospheres of hydrogen pressure. Under a protective nitrogen atmosphere, the reaction mixture is then filtered into a vessel containing 585 mg. of the ethyl ester of 5-nitro-1-methyl-2-imidazolyl-iminocarboxylic acid in 5 ml. of methanol with 0.25 ml. of 11.8N methanolic hydrochloric acid. After 24 hours at 20° C., the reaction product is vacuum-filtered and recrystallized from ethanol. Yield: 540 mg. of 5-methoxy-2-(5-nitro-1-methyl-2-imidazolyl)-benzimidazole, m.p. 202° C.

EXAMPLE 13

3 g. of 1,2-dinitro-4,5-diethoxybenzene is hydrogenated in 40 ml. of methanol with 500 mg. of Raney nickel in an autoclave at 120 atmospheres of hydrogen pressure. Under a protective nitrogen atmosphere, the reaction mixture is then filtered into a vessel containing 2.34 g. of the ethyl ester of 5-nitro-1-methyl-2-imidazolyl-iminocarboxylic acid in 20 ml. of methanol with 1.3 ml. of 12.5N methanolic hydrochloric acid. After 16 hours at 4° C., the reaction mixture is cooled to −70° C., vacuum-filtered, and washed with cold ethanol. Yield: 2.6 g. of 5,6-diethoxy-2-(5-nitro-1-methyl-2-imidazolyl)-benzimidazole, m.p. 198° C.

EXAMPLE 14

190 mg. of 4-nitro-1,2-phenylenediamine is treated as described in Example 1. The crude product is recrystallized from ethanol. Yield: 62 mg. of 5-nitro-2-(5-nitro-1-methyl-2-imidazolyl)-benzimidazole, m.p. 235° C.

EXAMPLE 15

182 mg. of 3,4-diaminobenzoic acid is treated as set forth in Example 1. However, the reaction mixture is allowed to stand for 24 hours at 20° C. Yield: 290 mg. of 2-(5-nitro-1-methyl-2-imidazolyl)-5-benzimidazole carboxylic acid, m.p. 310° C. The sodium salt is obtained from this compound by suspending it in water and mixing it with 1 equivalent of sodium hydroxide, and then evaporating the solution.

EXAMPLE 16

286 mg. of 5-trifluoromethyl-2-(2-hydroxyethylamino)aniline is treated as described in Example 1. The reaction mixture is, however, allowed to stand for 20 hours at 20° C. The crude product is recrystallized from an ethanol-acetone mixture. Yield: 280 mg. of 5-trifluoromethyl-1-(2-hydroxyethyl)-2-(5-nitro-1-methyl-2-imidazolyl)-benzimidazole, m.p. 174° C.

EXAMPLE 17

7.8 g. of 2-nitro-N-methylaniline is boiled for 60 hours with 450 mg. of palladium charcoal (10%) and 15.9 g. of 100% hydrazine hydrate in 120 ml. of 95% ethanol. After vacuum-filtering over kieselguhr, the reaction mixture is evaporated under a vacuum, and the residue is distilled by means of an oil pump. At 79°–81° C. and a pressure of 0.5 mm Hg, 4.14 g. of N-methyl-o-phenylenediamine are distilled over. 152 mg. of this compound is treated as set forth in Example 1. Yield: 184 mg. of 1-methyl-2-(5-nitro-1-methyl-2-imidazolyl)-benzimidazole, m.p. 163° C.

EXAMPLE 18

277 mg. of 2-(2-morpholinoethylamino)-aniline is treated as set forth in Example 1. Yield: 314 mg. of 1-(2-morpholinoethyl)-2-(5-nitro-1-methyl-2-imidazolyl)-benzimidazole as the hydrochloride, m.p. 237° C.

EXAMPLE 19

79 g. of 5-nitro-1-methyl-2-imidazolyl aldehyde oxime is introduced batchwise into 43 ml. of phosphorus oxychloride heated to 100° C. in such a manner that the reaction mixture just barely boils. After another 1.5 hours at 100° C., the reaction mixture is introduced into ice water, and the thus-precipitated 5-nitro-1-methyl-2-imidazolyl carboxylic acid nitrile (62 g.) is vacuum-filtered; m.p. 84°–85° C.

1.52 g. of this nitrile is heated in a bomb tube at 200° C. with 1.81 g. of o-phenylenediamine dihydrochloride for 2 hours. Preparative thin-layer chromatography of the reaction product with benzene-acetone 4:1 yields 320 mg. of 2-(5-nitro-1-methyl-2-imidazolyl)-benzimidazole, m.p. 257° C.

EXAMPLE 20

0.68 g. of 5-nitro-1-(2-acetoxyethyl)-2-imidazolyl aldehyde and 0.32 g. of o-phenylenediamine are boiled in 9 ml. of ethanol for 4 hours with the introduction of air. Cooling, vacuum-filtering, and digestion of the precipitate with ethanol results in 0.10 g. of 2-[5-nitro-1-(2-acetoxyethyl)-2-imidazolyl]-benzimidazole, m.p. 230° C.

EXAMPLE 21

2.86 g. of 1-(2-hydroxyethyl)-2-(5-nitro-1-methyl-2-imidazolyl)-benzimidazole are stirred in 40 ml. of pyridine with 1.91 g. of p-toluenesulfonchloride for 6 hours. After adding water, the reaction mixture is vacuum-filtered and recrystallized from ethanol. Yield: 1.55 g. of 1-(2-p-tosyloxyethyl)-2-(5-nitro-1-methyl-2-imidazolyl)-benzimidazole, m.p. 210° C.

EXAMPLE 22

2.86 g. of 1-(2-hydroxyethyl)-2-(5-nitro-1-methyl-2-imidazolyl)-benzimidazole are agitated in 10 ml. of thionyl chloride for 60 minutes. After evaporating to dryness, the reaction product is recrystallized from ethanol, thus obtaining 2.3 g. of 1-(2-chloroethyl)-2-(5-nitro-1-methyl-2-imidazolyl)-benzimidazole, m.p. above 250° C.

EXAMPLE 23

0.31 g. of 1-(2-chloroethyl)-2-(5-nitro-1-methyl-2-imidazolyl)-benzimidazole are boiled for 12 hours with 0.18 g. of morpholine in 50 ml. of dioxane. By evaporation and preparative thin-layer chromatography of the mixture, 50 mg. of 1-(2-morpholinoethyl)-2-(5-nitro-1-methyl-2-imidazolyl)-benzimidazole is obtained, the hydrochloride of which has a melting point of 237° C.

EXAMPLE 24

0.44 g. of 1-(2-tosyloxyethyl)-2-(5-nitro-1-methyl-2-imidazolyl)-benzimidazole is treated with morpholine, as described in Example 23. Yield after preparative layer chromatography: 70 mg. of 1-(2-morpholinoethyl)-2-(5-nitro-1-methyl-2-imidazolyl)-benzimidazole.

EXAMPLE 25

11 g. (78 millimols) of 5-nitro-1-ethylimidazole is heated in a sealed tube for 48 hours at 110° C. with 11.7 g. of paraformaldehyde in 57 ml. of dimethyl sulfoxide. After distilling off the volatile components at 1 mm Hg and a bath temperature of 100° C., the residue is recrystallized twice from benzene, thus obtaining 5.1 g. of 5-nitro-1-ethyl-2-hydroxymethylimidazole, m.p. 101° C. 3.42 g. of this compound is boiled for 8 hours in 113 ml. of benzene with 15 g. of lead(IV) acetate. The benzenic solution is cooled, filtered, washed neutral, and dried, and, after evaporation under a vacuum, 2.37 g. of 5-nitro-1-ethyl-2-imidazolyl aldehyde is obtained in the form of an oil.

5.08 g. of the aldehyde is dissolved in the hot state in 60 ml. of ethanol and mixed with a hot solution of 2.37 g. of hydroxylamine hydrochloride in 12 ml. of ethanol and 4.8 ml. of pyridine. After boiling for 3 minutes, 1.2 g. of water is added, the reaction mixture is stirred for one hour at 0° C., and vacuum filtered, thus obtaining 4.49 g. of the oxime, m.p. 232° C. 4.30 g. of this oxime is agitated for 3 hours at 100° C. with 1.14 ml of phosphorus oxychloride. By introducing the reaction mixture into water, 3.24 g. of 5-nitro-1-ethyl-2-imidazolyl carboxylic acid nitrile is obtained, m.p. 78° C.

3 g. of this nitrile is stirred for four hours at room temperature with 0.61 g. of potassium tert.-butanolate in 56 ml. of ethanol. Vacuum-filtering, concentrating the mother liquor, and again vacuum-filtering yields, in total, 1.95 g. of the ethyl ester of 5-nitro-1-ethyl-2-imidazolyl-iminocarboxylic acid, m.p. 51° C. This ester is treated with 1.66 g. of 2-(2-dimethylaminoethylamino)-aniline, as described in Example 1; prior to cooling and vacuum-filtering, the solution is somewhat concentrated. Yield: 1.5 g. of 1-(2-dimethylaminoethyl)-2-(5-nitro-1-ethyl-2-imidazolyl)-benzimidazole, as the hydrochloride, m.p. 243° C.

EXAMPLE 26

4.0 g. of 5-nitro-1-butyl-2-hydroxymethylimidazole is treated with lead(IV) acetate and worked up as set forth in Example 25, thus obtaining 3.03 g. of 5-nitro-1-butyl-2-imidazolyl aldehyde as an oil. The steps of reacting the compound to the corresponding oxime (m.p. 230° C.) with hydroxylamine; splitting off water with phosphorus oxychloride to obtaine the nitrile (oil); and production of the ethyl ester of 5-nitro-1-butyl-2-imidazolyl-iminocarboxylic acid (m.p. 60° C.) take place analogously to the reactions described in Example 25. By reacting 225 mg. of this compound with 168 mg. of 2-(2-dimethylaminoethylamino)-aniline, as in Example 25, 86 mg. of 1-(2-dimethylaminoethyl)-2-(5-nitro-1-butyl-2-imidazolyl)-benzimidazole is obtained as the hydrochloride, m.p. 221° C.

EXAMPLE 27

15 g. of o-nitrobromobenzene and 13 g. of 3-dibutylaminopropylamine are agitated with 15 g. of anhydrous sodium acetate for 7 hours at 135° C. The reaction mixture is taken up in 70 ml. of 6N hydrochloric acid and 80 ml. of water, the unreacted o-nitrobromobenzene is subjected to steam distillation, the distillation residue is rendered alkaline with potassium hydroxide solution, and extracted with ether. After distilling the residue of the ether extract, 12 g. of 2-(3-dibutylaminopropylamino)-nitrobenzene is obtained, b.p. 140°-160° C. at 0.1 mm Hg.

6.15 g. of this compound is boiled in 40 ml. of ethanol with 140 mg. of palladium on charcoal (10%) and 3 ml. of 80% hydrazine hydrate for 24 hours. Filtering and concentration of the reaction mixture yields 5.65 g. of 2-(3-dibutylaminopropylamino)-aniline in the form of an oil. 2 g. of this diamine are reacted with 1.45 g. of the ethyl ester of 5-nitro-1-methyl-2-imidazolyl-iminocarboxylic acid, as described in Example 1; however, the thus-obtained precipitate proved to be stronglycontaminated. In contrast thereto, the mother liquor, when mixed with 10% potassium hydroxide solution, yields 563 mg. of 1-(3-dibutylaminopropyl)-2-(5-nitro-1-methyl-2-imidazolyl)-benzimidazole, m.p. 79° C.

EXAMPLE 28

15 g. of o-nitrobromobenzene is reacted, analogously to Example 27, with 11 g. of 3-morpholinopropylamine, thus obtaining 9.23 g. of 2-(3-morpholinopropylamino)-nitrobenzene, b.p. 177°-187° C. at 0.1 mm Hg; this product solidifies in the flask (m.p. 41°-43° C.). Reduction with hydrazine palladium, as in Example 27, yields 4.7 g. of 2-(3-morpholinopropylamino)-aniline in the form of an oil, from 5.7 g. of the nitro compound. 2.95 g. of this diamine are reacted with 2.5 g. of the ethyl ester of 5-nitro-1-methyl-2-imidazolyl-iminocarboxylic acid, as described in Example 1. Yield: 3 g. of 1-(3-morpholinopropyl)-2-(5-nitro-1-methyl-2-imidazolyl)-benzimidazole, surprisingly in the form of the free base, m.p. 142° C.

EXAMPLE 29

3.5 mg. of 2-[5-nitro-1-(2-acetoxyethyl)-2-imidazolyl]-benzimidazole are boiled for 1 hour in 8 ml. of ethanol with 4 ml. of concentrated aqueous hydrochloric acid. After concentrating the reaction mixture to dryness, the residue is digested with methanol. After vacuum-filtering, 226 mg. of 2-[5-nitro-1-(2-hydroxyethyl)-2-imidazolyl]-benzimidazole is obtained, m.p. 217°-219° C.

EXAMPLE 30

500 mg. of 5-nitro-1-(2-acetoxyethyl)-2-imidazolyl carbonitrile are allowed to stand for 3 hours at 165° C.

in a bomb tube with 500 mg. of o-phenylenediamine hydrochloride. Preparative thin-layer chromatography of the product with methanol-chloroform 1 : 1 yields 80 mg. of 2-[5-nitro-1-(2-hydroxyethyl)-2-imidazolyl]-benzimidazole, m.p. 217°–219° C.

EXAMPLE 31

10.1 g. of o-nitrobromobenzene is reacted, analogously to Example 27, with 5.1 g. of 3-dimethylaminopropylamine, thus obtaining 6 g. of 2-(3-dimethylaminopropylamino)-nitrobenzene, b.p. 138°–141° C. at 0.1 mm Hg. By reducing 3.5 g. of this compound with hydrazine - palladium, 2.9 g. of 2-(3-dimethylaminopropylamino)-aniline is obtained in the form of an oil. 400 mg. of this diamine is reacted with the ethyl ester of 5-nitro-1-methyl-2-imidazolyl-iminocarboxylic acid, as described in Example 1, to obtain 407 mg. of 1-(3-dimethylaminopropyl)-2-(5-nitro-1-methyl-2-imidazolyl)-benzimidazole hydrochloride, m.p. 250° C.

EXAMPLE 32

4.15 g. of 2-(2-pyrrolidinoethylamino)-aniline is reacted with 4 g. of 5-nitro-1-methyl-2-imidazolyl-iminocarboxylic acid ester, as described in Example 1; however, after stirring the reaction mixture at room temperature, it is made alkaline with aqueous solution of potassium hydroxide. The reaction mixture is then dissolved in methanolic hydrochloric acid and again precipitated with aqueous solution of sodium hydroxide, thus obtaining 1.15 g. of 1-(2-pyrrolidinoethyl)-2-(5-nitro-1-methyl-2-imidazolyl)-benzimidazole, m.p. 120°–121° C.

EXAMPLE 33

17.2 g. of 4-chloro-3-nitrotoluene, 9 g. of 2-dimethylaminoethylamine, and 21.5 g. of anhydrous sodium carbonate are agitated for 7 hours at 135° C. Excess starting material is removed by steam distillation. The distillation residue is extracted with chloroform, the chloroform solutions are dried, filtered, and concentrated under a vacuum. By distilling the residue at 0.05 mm Hg and 133°–137° C., 10.5 g. of 3-nitro-4-(2-dimethylaminoethylamino)-toluene is obtained, m.p. 59° C. 3.5 g. of this compound is reduced as described in Example 27, and 3 g. of crude 3-amino-4-(2-dimethylaminoethylamino)-toluene is thus obtained. 400 mg. of this compound is reacted with 400 mg. of the ethyl ester of 5-nitro-1-methyl-2-imidazolyliminocarboxylic acid, as described in Example 1, thus producing 172 mg. of 1-(2-dimethylaminoethyl)-5-methyl-2-(5-nitro-1-methyl-2-imidazolyl)-benzimidazole hydrochloride, m.p. 249°–251° C.

EXAMPLE 34

1.7 g. of 5-nitro-1-methyl-2-imidazolyl carboxylic acid and 1.08 g. of o-phenylenediamine are heated for 40 minutes in a bomb tube to 180° C. in 10 ml. of 25% hydrochloric acid. After evaporating the reaction mixture to dryness and column chromatography on 100 g. of silica gel with methanol-chloroform 1 : 1, 120 mg. of 2-(5-nitro-1-methyl-2-imidazolyl)-benzimidazole is obtained, m.p. 257° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 2-(5-nitro-2-imidazolyl)-benzimidazole of the formula

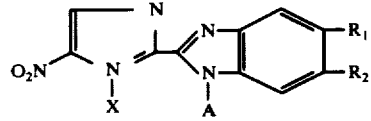

wherein $R_1$ and $R_2$ each are hydrogen, halogen, alkyl of 1 to 4 carbon atoms, alkoxy of 1 to 4 carbon atoms, nitro, trifluoromethyl or carboxy; A is hydroxyalkyl of 2 to 5 carbon atoms or an acyl ester thereof of an alkanoic acid of up to 12 carbon atoms or of a physiologically acceptable benzoic or naphthoic acid of up to 12 carbon atoms which is unsubstituted or mono-substituted by lower n-alkyl, lower n-alkoxy, hydroxy or amino, disubstitued by lower n-alkyl, lower n-alkoxy or mono-amino-mono-hydroxy or tri-substituted by lower n-alkyl or lower n-alkoxy, haloalkyl of 2 to 5 carbon atoms, or aminoalkyl of the formula

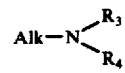

wherein Alk is alkyl of 2 to 5 carbon atoms and $R_3$ and $R_4$ each are alkyl of 1 to 5 carbon atoms, or, together with the N-atom, pyrrolidino, piperidino, homopiperidino, piperazino, morpholino, or one of said heterocyclic groups substituted on a ring carbon atom by alkyl of 1 to 5 carbon atoms, or piperazino substituted on the 4-position nitrogen atom by piperazino substituted on the 4-position nitrogen atom by alkyl of 1-5 carbon atoms, hydroxyalkyl of 2-5 carbon atoms or an alkanoyloxy ester thereof of 1-5 carbon atoms; and X is alkyl of 1 to 5 carbon atoms; or a physiologically acceptable salt thereof.

2. A compound according to claim 1 wherein A is hydroxyethyl or an ester thereof as defined therein.

3. A compound according to claim 1 wherein A is aminoalkyl as defined therein.

4. A compound according to claim 3 wherein X is methyl.

5. A compound according to claim 4 wherein A is dialkylaminoalkyl.

6. A compound according to claim 4 wherein A is pyrrolidinoalkyl.

7. A compound according to claim 4 wherein A is morpholinoalkyl.

8. A compound according to claim 4, 1-(2-dimethylaminoethyl)-2-(5-nitro-1-methyl-2-imidazolyl)-benzimidazole hydrochloride.

9. A compound according to claim 4, 1-(2-dimethylaminoethyl)-2-(5-nitro-1-ethyl-2-imidazolyl)-benzimidazole hydrochloride.

10. A compound according to claim 4, 1-(2-dimethylaminoethyl)-2-(5-nitro-1-methyl-2-imidazolyl)-5-methylbenzimidazole hydrochloride.

11. A compound according to claim 4, 1-(2-pyrrolidylethyl)-2-(5-nitro-1-methyl-2-imidazolyl)-benzimidazole.

12. A compound according to claim 4, 1-(3-morpholinopropyl)-2-(5-nitro-1-methyl-2-imidazolyl)-benzimidazole.

13. A compound according to claim 4, 1-(3-dimethylaminopropyl)-2-(5-nitro-1-methyl-2-imidazolyl)-benzimidazole hydrochloride.

14. A 2-(5-nitro-2-imidazolyl)-benzimidazole of the formula

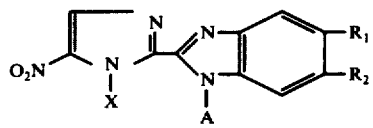

wherein $R_1$ and $R_2$ each are hydrogen, halogen, alkyl of 1 to 4 carbon atoms, alkoxy of 1 to 4 carbon atoms, nitro, trifluoromethyl and carboxy; A is H, alkyl of 1–5 carbon atoms, hydroxyalkyl of 2 to 5 carbon atoms or an acyl ester thereof of an alkanoic acid of up to 12 carbon atoms or of a physiologically acceptable benzoic or naphthoic acid of up to 12 carbon atoms which is unsubstituted or mono-substituted by lower n-alkyl, lower n-alkoxy, hydroxy or amino, disubstituted by lower n-alkyl, lower n-alkoxy or mono-amino-monohydroxy or trisubstituted by lower n-alkyl or lower n-alkoxy, haloalkyl of 2 to 5 carbon atoms, phenyl or aminoalkyl of the formula

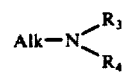

wherein Alk is alkyl of 2 to 5 carbon atoms and $R_3$ and $R_4$ each are alkyl of 1 to 5 carbon atoms, or, together with the N-atom, pyrrolidino, piperidino, homopiperidonio or morpholino, piperazino, the corresponding heterocyclic rings substituted on a ring carbon atoms by alkyl of 1 to 5 carbon atoms, or piperazino substituted on the 4-position nitrogen atom by alkyl of 1–5 carbon atoms, hydroxylaklyl of 2–5 carbon atoms or an alkanoyloxy ester thereof of 1-5 carbon atoms; and X is hydroxyalkyl of 2 to 5 carbon atoms or an ester thereof of an alkanoic acid of up to 12 carbon atoms or of a physiologically acceptable benzoic or naphthoic acid of up to 12 carbon atoms which is unsubstituted or monosubstituted by lower n-alkyl, lower n-alkoxy or mono-amino-mono-hydroxy or trisubstituted by lower n-alkyl or lower n-alkoxy; or a physiologically acceptable salt thereof.

* * * * *